US012788489B2

(12) United States Patent
Murphy

(10) Patent No.: US 12,788,489 B2
(45) Date of Patent: Nov. 10, 2026

(54) SYSTEM AND PROCESS FOR PREOPERATIVE SURGICAL PLANNING

(71) Applicant: Michael P. Murphy, Downers Grove, IL (US)

(72) Inventor: Michael P. Murphy, Downers Grove, IL (US)

(*) Notice: Subject to any disclaimer, the term of this patent is extended or adjusted under 35 U.S.C. 154(b) by 681 days.

(21) Appl. No.: 17/895,525

(22) Filed: Aug. 25, 2022

(65) Prior Publication Data

US 2024/0065763 A1 Feb. 29, 2024

(51) Int. Cl.
*A61B 34/10* (2016.01)
*G06N 20/00* (2019.01)
*A61B 34/00* (2016.01)

(52) U.S. Cl.
CPC ............. *A61B 34/10* (2016.02); *G06N 20/00* (2019.01); *A61B 2034/252* (2016.02)

(58) Field of Classification Search
CPC ... A61B 34/10; A61B 2034/252; G06N 20/00
USPC .......................................................... 382/128
See application file for complete search history.

(56) References Cited

U.S. PATENT DOCUMENTS 9,129,054 B2* 9/2015 Nawana ............... A61B 5/4848
2014/0013565 A1* 1/2014 MacDonald ........... G16H 50/70 703/11
2019/0380792 A1* 12/2019 Poltaretskyi .......... G06F 3/0482
2021/0378752 A1* 12/2021 Paul ....................... A61B 34/20
2022/0084652 A1* 3/2022 Daley ..................... A61B 17/17
2024/0065766 A1* 2/2024 Chaoui ................. A61F 2/4081
2024/0115324 A1* 4/2024 Mosnier ............. A61B 17/7032
2024/0374316 A1* 11/2024 Casey ..................... A61B 34/10

FOREIGN PATENT DOCUMENTS

CN 113892146 A * 1/2022 ............... G06N 5/01
IN 202131034547 A * 8/2021 ............. A61B 34/10
IN 202131034647 A * 8/2021 ............. A61B 34/10

OTHER PUBLICATIONS

Lambrechts et al. Artificial Intelligence Based Patient-Specific Preoperative Planning Algorithm for Total Knee Arthroplasty. Frontiers in Robotics and AI, 9. https://doi.org/10.3389/frobt.2022.840282 (Year: 2022).*

(Continued)

*Primary Examiner* — Jennifer Mehmood
*Assistant Examiner* — Eric James Shoemaker
(74) *Attorney, Agent, or Firm* — The Rapacke Law Group, P.A.; Andrew S. Rapacke; Kenneth F. Brooks

(57) ABSTRACT

A system and method for surgical planning includes an electronic device with an interface for a user to input patient information, which may include an image demographic information and a server receiving and storing the preoperative data in a data storage. An application includes an implementation of an artificial intelligence model, which is executed using the data as input to generate a surgical plan specific to the surgeon executing this plan. The preoperative plan can include a list of medical instruments for use during the surgical procedure and/or a list of surgical steps to perform the surgical procedure Information about the surgical procedure is captured during and/or after the surgical procedure. The operative data is stored in the data storage. The operative data is used to develop insights for the artificial intelligence model.

20 Claims, 4 Drawing Sheets

(56) References Cited

OTHER PUBLICATIONS

Lambrechts A, Wirix-Speetjens R, Maes F, Van Huffel S. Artificial Intelligence Based Patient-Specific Preoperative Planning Algorithm for Total Knee Arthroplasty. Front Robot AI. Mar. 8, 2022;9:840282. doi: 10.3389/frobt.2022.840282. (Year: 2022).*

* cited by examiner

SYSTEM AND PROCESS FOR PREOPERATIVE SURGICAL PLANNING

TECHNICAL FIELD

The embodiments generally relate to preoperative planning, and more particularly relate to preoperative planning for surgical cuts, orientation of implants, and necessary implant sizes in surgery.

BACKGROUND

Orthopedic surgeons and other healthcare professionals commonly rely on surgical guidance techniques that can commonly be classified into two categories: preoperative templating that enables pre-surgical planning, and intraoperative guidance for placement and orientation of surgical instruments within a patient. Preoperative templating enables surgical planning by commonly using digital or hard copy radiographic images or similar x-ray-type, frequently scaled according to an object of a known size. This may involve three-dimensional imaging (e.g. computed tomography or magnetic resonance imaging) or two-dimensional imaging (e.g. x-ray, ultrasound). Commonly, a spherical ball marker of known size is placed and appears in the image for scaling reference. The spherical ball might not be needed in images where the scaling factor would already be known and may be estimated in cases where the calibration marker is not present. Using a radiopaque contour of the bone and other tissue in an x-ray image, preoperative surgical cuts, implants, and orientation may be planned.

Additionally, certain patient factors have shown to be predictive of necessary operative needs. For example, patient demographic factors have shown to be beneficial in predicting the size of an implanted total knee arthroplasty femur and tibia component. The same has been shown for total hip arthroplasty femur and acetabular cup components. Patient shoe size has also been shown to be predictive of required implant size. Further, several patient factors have shown to increase the patient risk for any of a number of complications. These factors may lead the surgeon to adjust implant choice, surgical cuts, and orientation of the implants.

SUMMARY

This summary is provided to introduce a variety of concepts in a simplified form that is further disclosed in the detailed description of the embodiments. This summary is not intended to identify key or essential inventive concepts of the claimed subject matter, nor is it intended for determining the scope of the claimed subject matter.

The embodiments provided herein relate to systems and processes for surgical planning and/or assessment of the surgery. These processes can include receiving, via input from a user, data relating to and/or that involves patient information and/or images; storing the data in data storage (e.g. a database stored in computer memory); generating an operative plan for a surgical procedure and/or assessment of the surgical procedure by executing an artificial intelligence model using the data as input to the artificial intelligence model; capturing data resulting from a surgical procedure and/or feedback from the user; storing the data in the data storage; developing insights for the artificial intelligence model based on the stored data; and updating parameters of the artificial intelligence model based on the insights, wherein the insights are values for updating the parameters of the artificial intelligence model. As such, the stored data can be used in a feedback loop for future artificial intelligence modeling. According to one or more aspects, the stored data comprises at least one of an image or patient information. According to one or more aspects, the operative plan for a surgical procedure comprises a list of medical instruments for use during the surgical procedure. According to one or more aspects, the assessment of the surgical procedure includes the position, orientation, and/or size of at least one of the implants used in the surgical procedure, the prosthesis used in the surgical procedure, and/or a cut or incision occurring during the surgical procedure.

In one aspect, at least one of a server and/or an electronic device includes the data storage and executing the artificial intelligence model occurs on or via at least one of the server and/or the electronic device. The surgical procedure includes performing a surgical incision (or more generally, cutting tissue) for receiving at least one of an implant or a prosthesis.

In one aspect, the data corresponds to at least one of position, orientation, and/or size of at least one of the implant used in the surgical procedure, the prosthesis used in the surgical procedure, or a cut occurring during the surgical procedure. According to one or more aspects, the data comprises at least one of an image or patient information.

In one aspect, the artificial intelligence model is trained to generate a preoperative plan at least based on training data; and the preoperative plan comprises a list of medical instruments for use during the surgical procedure and/or a list of surgical steps to perform the surgical procedure. Each surgical step of the list of surgical steps can be associated with one or more of the medical instruments from the list of medical instruments.

In one aspect, the artificial intelligence model is trained to generate an operative assessment at least based on training data; and the operative assessment corresponds to at least one of position, orientation, and/or size of at least one of the implant used in the surgical procedure, the prosthesis used in the surgical procedure, or a cut occurring during the surgical procedure. According to one or more aspects, the training data comprises at least one of an image or patient information.

In one aspect, a computerized surgical planning system comprises an electronic device with an interface configured to receive input from a user, the input including data; a server that receives the data via a network; a data storage (e.g. a database stored in computer memory) that stores the data; computer memory storing an application; a processor that executes the application and causes the system to: receive, via input from a user, data; store the data in a data storage; generate an operative plan for a surgical procedure and/or assessment of the surgical procedure by executing an artificial intelligence model using the data as input to the artificial intelligence model; capture data resulting from a surgical procedure and/or from user feedback; store the data in the data storage; develop insights for the artificial intelligence model based on the data; and update parameters of the artificial intelligence model based on the insights, wherein the insights are values for updating the parameters of the artificial intelligence model.

BRIEF DESCRIPTION OF THE DRAWINGS

A complete understanding of the present embodiments and the advantages and features thereof will be more readily understood by reference to the following detailed description when considered in conjunction with the accompanying drawings wherein.

Like reference numerals refer to like parts throughout the several views of the drawings.

DETAILED DESCRIPTION

Figure 1:
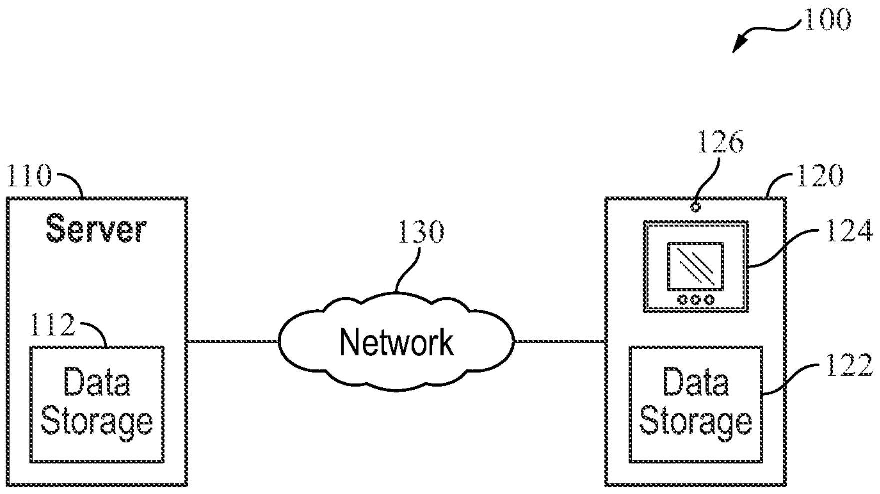
FIG. 1 illustrates a block diagram of a preoperative planning system, according to one or more aspects.

Any specific details of embodiments are used for demonstration purposes only, and no unnecessary limitations or inferences are to be understood therefrom.

Before describing in detail exemplary embodiments, it is noted that the embodiments reside primarily in combinations of components and procedures related to the apparatus. Accordingly, the apparatus components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

As used herein, relational terms, such as "first" and "second," "top" and "bottom," and the like, may be used solely to distinguish one entity or element from another entity or element without necessarily requiring or implying any physical or logical relationship, or order between such entities or elements. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific steps, process order, dimensions, component connections, and other physical characteristics relating to the embodiments disclosed herein are not to be considered as limiting, unless the claims expressly state otherwise. The use or mention of any single element contemplates a plurality of such element, and the use or mention of a plurality of any element contemplates a single element (for example, "a device" and "devices" and "a plurality of devices" and "one or more devices" and "at least one device" contemplate each other), regardless of whether particular variations are identified and/or described, unless impractical, impossible, or explicitly limited.

Shown throughout the figures, the exemplary and non-limiting embodiments generally relate to preoperative planning, and more particularly relate to systems and processes for preoperative surgical planning.

In various embodiments no user-input is necessary aside from uploading patient information and/or images. As described herein, embodiments include programs that can use an x-ray image/image file and identify the implant(s) that would fit the contour of the individual patient's bone(s) the best. As described herein, embodiments separately include programs that can use an x-ray image/image file and identify the position that/those implant(s) implants are in, and/or to plan for and/or map the orientation/position of the surgical cuts. All of this can be performed without requiring the user to independently and/or manually select between implant sizes or position/orient the implant. When user input is provided, the program may develop insights from user input related to the implant sizes and/or position/orientation or the position/orientation of the surgical cuts.

FIG. 1 illustrates a block diagram of a surgical planning system 100. The surgical planning system 100 includes a server 110 and an electronic device 120 communicatively connected to each other via a network 130. The server 110 can be a local and/or remote server, a virtual or cloud server (whether shared or dedicated). The electronic device 120 can be any type of appropriate electronic device including smartphones, mobile phones, tablets, laptops, desktop computers, portable screen displays, personal digital assistants, terminals, electronic devices dedicated to operative planning or assessment, touchscreen displays or devices, and/or the like. According to one or more aspects, one or more servers 110 are connected to one or more electronic devices 120 via one or more networks 130.

The server 110 has a server data storage 112. The electronic device 120 has a device data storage 122. Data storage (whether the server data storage 112, the device data storage 122, or both) can be local, remote, cloud-based, shared, dedicated, and/or the like, and can be a database, a data warehouse, a data lake, a data repository, a file storage, RAM, ROM, flash memory, and/or the like. According to one or more aspects, only the server 110 has a data storage, only the electronic device 120 has a data storage, or neither the server 110 or the electronic device 120 has data storage with the data storage residing separately from the server 110 and the electronic device 120. According to one or more aspects, the data storage 112 resides outside of the server 110, or the data storage 112 resides within the server 110. In some embodiments server 110 can be communicatively coupled with a cloud platform via network 130. The cloud platform can include one or more cloud servers, cloud database storage, cloud computing portion, and others.

The network 130 includes any technically feasible type of communications network that allows data to be exchanged between the electronic device 120 and external entities or devices, such as a web server, a database, or another networked computing device, including the server 110 and/or the data storage 112. For example, network 130 may include a wide area network (WAN), a local area network (LAN), a wireless or Wi-Fi® network, Bluetooth®, and/or the Internet, among others.

In some embodiments the electronic device 120 has an interface 124 and a camera 126, or access to images (of any format) via data storage 122. Electronic device 120 can be a mobile device that may upload images (e.g. x-rays image files in DICOM format, jpegs, pngs, and/or others) that are captured via a camera 126. Additionally or alternatively, electronic device may upload these images/image files from its own data/file storage 122. In various embodiments, users who may have a laptop or other electronic device without an operatively coupled camera may also use the application, so long as they have access to image files. The interface 124 can be any input and/or output means for computer and electronic devices, including mouse, keyboard, keypad, virtual keyboard, touchscreen, displays, graphical user interfaces, monitors, speakers, knobs, ports (e.g. USB ports, HDMI, Ethernet, Thunderbolt®, SD card, PCI card, Firewire, and/or the like), physical or displayed buttons, LED's, switches, and/or the like. The interface 124 and/or the camera 126 are configured to receive input from a user (for example, user 210 of FIG. 2, discussed below). The input from the user can include data of a patient and/or image. Data can include images/image files and/or patient information. The images/image files include patient photos, patient radiological imaging (e.g. MRI, X-Ray, CT scans, and/or the like), photos and/or drawings and/or images and/or diagrams and/or schematics and/or structural parameters of medical instruments (e.g. implants, prosthetics, virtual and/or robotic instruments, scissors, shears, clamps, hemostats, plasma, fluids, medicaments, orthopedic screws, plates, gauze, temporary bone screws, and/or the like), scale information, and/or the like. The scale information is a reference, parameter, and/or indicator that specifies the scale of distances and/or objects in an image. In some embodiments images can be scaled based on a set value (e.g. an x-ray could be scaled to 115% of the original with no reference object). The images/image files can include audio and/or can be 2D (2-dimensional), 3D (3-dimensional), 2D with depth information, 2D video, 3D video (for example, holographic video), animation, sequential images, and/or the like. Generally, the camera 126 captures the images. For example, the camera 126 can be pointed to multiple body parts of the patient to capture images of the areas that will undergo the surgical procedure. Additionally or alternatively, the camera 126 can be pointed to the X-Ray or 3D images to capture images of the areas that will undergo the surgical procedure, or to develop an assessment of these images via the artificial intelligence program 338. There are images that require specialized equipment, such as MRI and X-Ray images; thus, the electronic device 120 is configured to receive images from sources other than the interface 124 and the camera 126, such as images stored in USB or similar media, and images received via the network 130, including images sent to the electronic device 120 directly and/or stored in the data storage (including data storage 112 and/or 122). For example, a radiologist might send images to an email or to the server 110 through the network 130 for the system 100 to automatically store the images in the data storage 112.

The patient information includes a patient's medical information, demographic information, personal information, such as age, gender, ethnicity, height, weight, race, side and/or location being operated on, shoe size, vaccination records, diagnosis, medical history, current and/or previous medications, family medical history, prior surgical procedures and/or prior surgical procedure outcomes, prognosis for prior and/or current treatment, the current pending surgical procedure, medical instruments for the surgical procedure, diseases, syndromes, medical conditions, allergies, medical preferences (living will, medical directives, no use of anesthetics or drugs, preferred use of anesthetics), and/or the like.

The surgical planning system 100 may be configured to execute a preoperative surgical planning application (such as the surgical planning application 334 of FIG. 3, discussed below) that generates a preoperative plan for a surgical procedure. This application contains an artificial intelligence module (such as the artificial intelligence module 338 of FIG. 3, discussed below). The application, when executed, operates the interface 124 to receive the data, stores the data to and/or receives the data from the data storage (the server data storage 112, the device data storage 122, or another data storage), and inputs the data to the artificial intelligence model. According to one or more aspects, the application is configured to generate modified data by normalizing and/or standardizing the data, and then inputs the modified data to the artificial intelligence model. According to one or more aspects, the application is configured to generate an operative plan for a surgical procedure or assessment of a surgical procedure by executing the artificial intelligence model using the data as input to the artificial intelligence model. Using the data as input contemplates using the modified data as input. In one aspect, the operative plan for a surgical procedure involves an artificial intelligence model 338 that is trained to generate a preoperative plan at least based on training data; and the preoperative plan comprises a list of medical instruments 224 for use during the surgical procedure and/or a list of surgical steps to perform the surgical procedure. Each surgical step of the list of surgical steps can be associated with one or more of the medical instruments from the list of medical instruments. In one aspect, the assessment of a surgical procedure involves an artificial intelligence model 338 that is trained to generate an operative assessment at least based on training data; and the operative assessment corresponds to at least one of position, orientation, and/or size of at least one of the implant 224 used in the surgical procedure, the prosthesis used in the surgical procedure, or a cut occurring during the surgical procedure. According to one or more aspects, the training data comprises at least one of an image or patient information.

In various embodiments the systems and methods are operable to develop insights in and through the artificial intelligence model by capturing data resulting from the procedure and/or from user feedback. In other words, the system does not require direct data from within the operating room. In various instances, data can be entered by a user who is inputting information about operating room occurrences, procedures, and/or related information.

The preoperative plan can include a list of steps to follow during a surgical procedure and/or a list of medical instruments to be used during a surgical procedure. According to one or more aspects, the list of steps also includes steps that may be performed if there are complications, delays, inefficiencies, and/or other problems during the surgical procedure. According to one or more aspects, the list of medical instruments also includes instruments that may be used if there are complications, delays, inefficiencies, and/or other problems during the surgical procedure. Each medical instrument in the list of medical instruments can be associated with one or more of the steps of the list of steps of the surgical procedure. Each step in the list of steps of the surgical procedure includes the location, position, direction, length, orientation, shape, depth, form and/or order of use of the surgical incision, the implant, the prosthetic, and/or any other medical instruments. As a nonlimiting example, a user can upload a patient's information 220 from their electronic device 120 through the network 130 to the server 110. This server 110 will store the data in the data storage 112 and execute the artificial intelligence model and deliver the resulting information back to the user 210 through the electronic device 120 (e.g. via a display). As a nonlimiting example, the preoperative plan may include features such as size of implants, type of implant needed, orientation/angle of the surgical cut, position of the surgical cut. The server 110 may also be configured to deliver information via the network 130 to multiple parties in need of the information. As a nonlimiting example, the user 210 will receive the information from their electronic device 120, while a separate user may also be notified as well. As a nonlimiting example, a sales representative of a device may additionally be notified of a user's 210 surgical plan.

The operative assessment can include features such as size of implants, type of implant, orientation/angle of the implant, orientation/angle of the surgical cut, position of the implant, or position of the surgical cut. As a nonlimiting example, a user can upload a patient's X-Ray image and/or data using their device 120 via their data storage 122 or camera 126/226. The device 120 may communicate with the server 110 via the network 130, and the artificial intelligence model 338 may determine the orientation/angle of the implant based on the uploaded image and/or data, and display this information to the user 124. In this example, the operative assessment may be performed post-operatively (after the implant is already within the patient), intra-operatively or during surgery, or preoperatively in the setting of a planned revision surgery. The user, or another user, may provide feedback regarding the orientation, where the artificial intelligence model 338 may develop insights based on this feedback. As an additional nonlimiting example, the user may use the operative assessment for feedback regarding the orientation of a surgical cut. In this subsequent example, the user can upload a picture of their device 120 during the surgery via their data storage 122 or camera 126/226. The device 120 may communicate with the server 110 via the network 130, and the artificial intelligence model 338 may determine the orientation/angle of the surgical cut and display this information to the user 124. The user may provide feedback regarding the orientation, or a subsequent user may provide the same feedback, where the artificial intelligence model 338 may develop insights based on this feedback.

Figure 2:
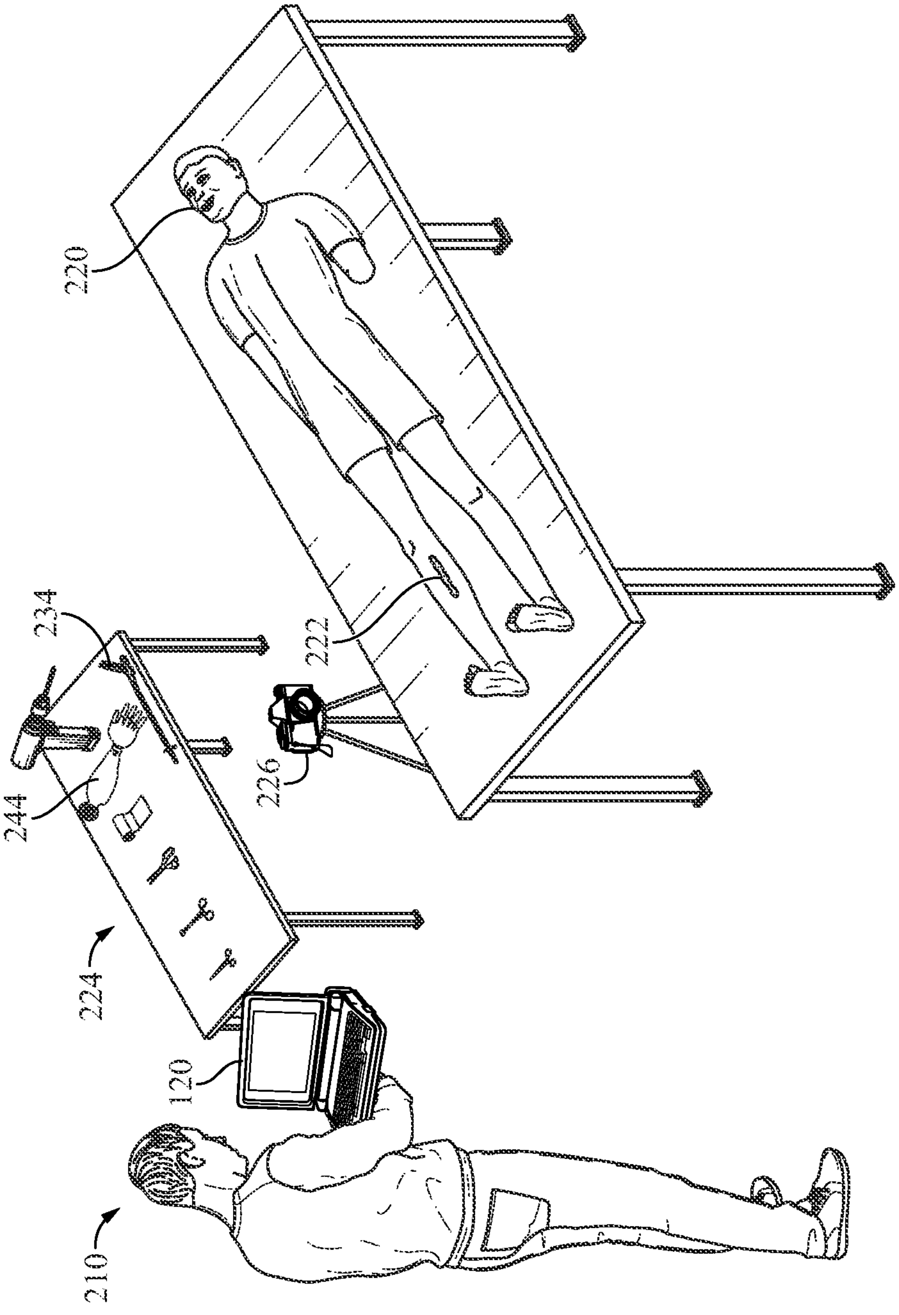
FIG. 2 illustrates a perspective view of an environment with a user make use of an electronic device of a preoperative planning system with a patient, according to one or more aspects.

FIG. 2 illustrates a user 210 using the electronic device 120 and a patient 220. The electronic device 120, via the interface 124 (shown in FIG. 1), is configured to receive data of a patient as input from a user 210. The user 210 can be a medical doctor, a nurse, a technician, a scribe, a medical sales representative, a medical assistant, and/or a medical professional who inputs the data to the application through operation of the electronic device 120. In other words, the electronic device 120 is the hardware and the application is the software that runs on the hardware (runs on the electronic device 120), and they (the hardware and the software) are configured to present a user interface display to the user 210 through the interface 124 (shown in FIG. 1) that enables the user 210 to input the data. According to one or more aspects, the application runs on the server 110 and/or on the electronic device 120 and is configured to receive commands as input from the user 210, through the interface 124, directing the application to receive data that can be (1) input from the user 210, (2) at the server 110, and/or (3) at the electronic device 120. If the application, to execute, needs data already stored, it can grab or otherwise access the data from data storage (including server data storage 112, device data storage 122, and/or other data storage). The application causes the data to be stored in the data storage 112, the data storage 122, and/or another data storage.

In some embodiments the user 210 may involve multiple people. As a nonlimiting example, the user 210 may upload a photo of an x-ray via the network 130 to the server data storage 112. Then, a technician may provide feedback such that the artificial intelligence model 338 may develop insights based on this feedback. In this setting, the subsequent user (in this example, the technician) need only have access to the stored data 112.

In some embodiments medical instruments 224 and a camera 226 can be located in close proximity to the patient 220. The medical instruments 224 include, for example, implants, prosthetics, virtual and/or robotic instruments, scissors, shears, clamps, hemostats, plasma, fluids, medicaments, orthopedic screws, plates, gauze, temporary bone screws, and/or the like. The patient 220 has a surgical incision 222.

The camera 226, which incorporates the characteristics of the camera 126, is physically separate from the electronic device 120. According to one or more aspects, the camera 226 is communicatively connected to the electronic device 120 through the network 130. The camera 226 is configured, positioned, and/or oriented to capture operative data before, during, and/or after the surgical procedure. According to one or more aspects, the camera 126 of the electronic device 120 is configured, positioned, and/or oriented to capture operative data before, during, and/or after the surgical procedure either by itself with or without the camera 226 or in coordination with the camera 226 to generate perspective information, scale information, coordinate images and or video views, and/or generate 3D images and/or video. According to one or more aspects, the electronic device 120, the camera 126, and/or the camera 226 capture audio.

Figure 3:
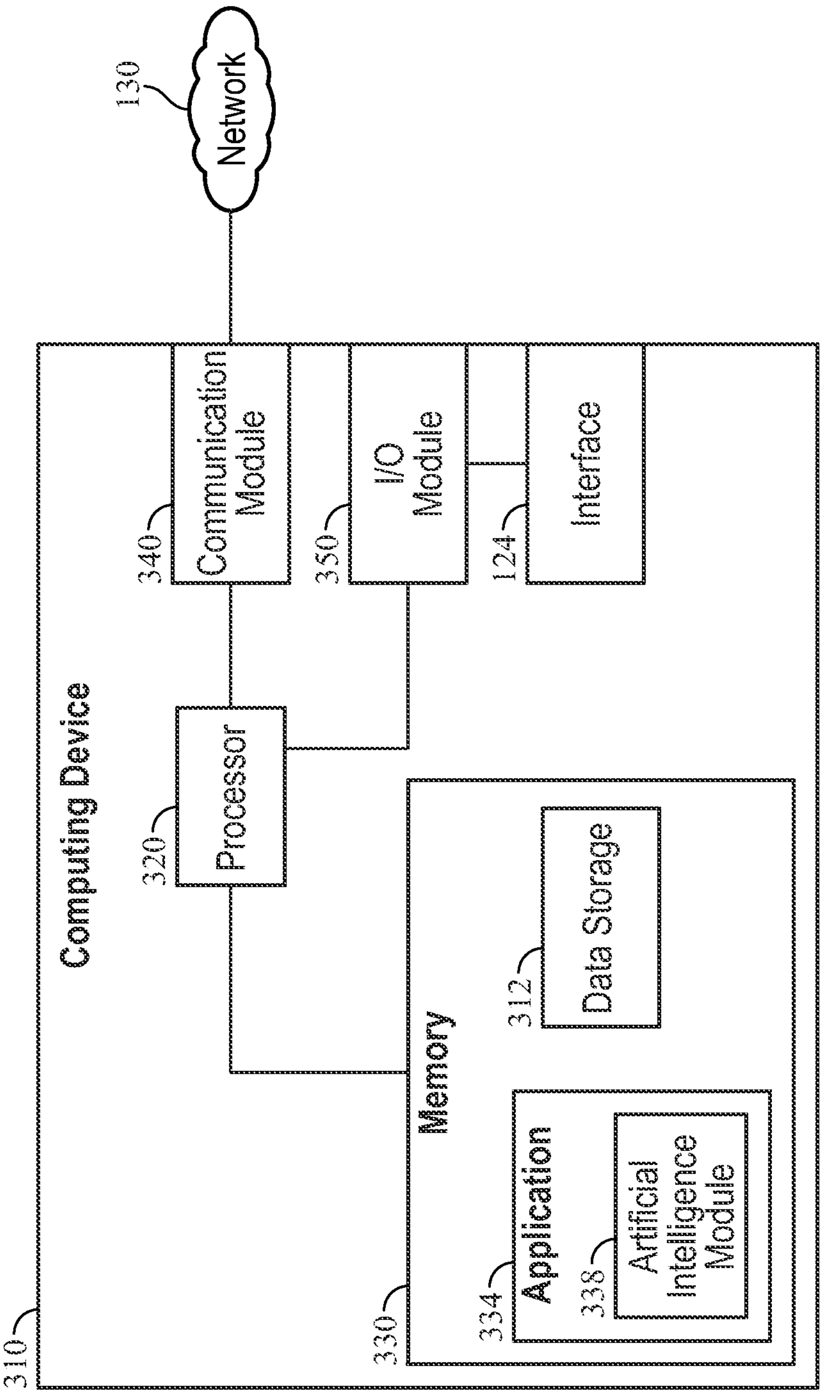
FIG. 3 illustrates a block diagram of a computing device of a preoperative planning system, according to one or more aspects.

FIG. 3 illustrates a block diagram of a computing device 310. The server 110 and/or the electronic device 120 incorporate the characteristics and features of the computing device 310. The computing device 310 includes a processor 320, a memory 330, a communication module 340, an input/output module 350 (I/O module 350), and a data storage 312. According to one or more aspects, the computing device 310 includes the interface 124, as shown in FIG. 3, or does not include an interface.

A processor 320 suitable for the execution of a computer program (such as the application 334 and/or the artificial intelligence module 338) include both general and special purpose microprocessors and any one or more processors of any digital computing device. The processor 320 will receive instructions and data from a read-only memory or a random-access memory or both. The essential elements of a computing device are a processor for performing actions in accordance with instructions and one or more memory devices for storing instructions and data. Generally, a computing device will also include, or be coupled to receive data from or transfer data to, or both, one or more mass storage devices for storing data, e.g., magnetic, magneto-optical disks, or optical disks; however, a computing device need not have such devices. Moreover, a computing device can be embedded in another device, e.g., a mobile telephone, a smartphone, a tablet, a laptop, electronic medical devices, a digital camera, a personal digital assistant (PDA), a mobile audio or video player, a game console, a Global Positioning System (GPS) receiver, or a portable storage device (e.g., a universal serial bus (USB) flash drive).

The processor 320 is communicatively coupled to the memory 330. The memory 330 includes an application 334. The application 334 configured to implement certain aspects described herein, and a data storage 312. The server data storage 112 and/or the device data storage 122 incorporate the characteristics and features of the data storage 312. The data storage 312 stores various data accessible by the application 334, including patient information, images, pre-operative data, intraoperative data, and post-operative data. In one aspect, the application instructions 334 may include software elements corresponding to one or more of the various aspects described herein. For example, application 334 may be implemented in various aspects using any desired programming language, scripting language, or combination of programming languages and/or scripting languages (e.g., C, C++, C#, JAVA®, JAVASCRIPT®, PERL®, etc.). As another example, the application 334 includes an artificial intelligence module 338.

The artificial intelligence module 338 may contain, call, and/or be implemented as one or more of a reactive machine, a limited memory machine, a theory of mind machine, a self-aware machine, an artificial narrow intelligence machine, an artificial general intelligence machine, an artificial super intelligence machine, machine learning structures and/or algorithms (including supervised learning, unsupervised learning, reinforcement learning, semi-supervised learning, self-supervised learning, multi-instance learning, inductive learning, deductive learning, transductive learning, multi-task learning, active learning, online learning, transfer learning, ensemble learning, regression, linear regression, logistic regression, classification, decision tree, SVM, Naïve Bayes, kNN, K-Means, random forest, dimensionality reduction, gradient boosting, GBM, XGBoost, Light GBM, CatBoost, and/or the like), a neural network (including a deep neural network, a feedforward network, a multilayer perceptron, a convolutional neural network, a radial basis functional neural network, a recurrent neural network, a long short-term memory, sequence-to-sequence, a modular neural network, and/or the like), and/or the like. The artificial intelligence module 338 learns and/or is trained with data as input and operative data as output. The input data includes patient information and/or images. The output data corresponds to size of implants, type of implant, orientation/angle of the implant, orientation/angle of the surgical cut, position of the implant, or position of the surgical cut.

The processor 320 is communicatively connected to the communication module 340. The communication module 340 is communicatively connected to the network 130. The communication module 340 is configured to allow data to be exchanged between the computing device 310 and other devices attached to a network 130, such as other computer systems, or between nodes of the system 100. According to one or more aspects, the communication module 340 supports communication via wired or wireless general data networks, such as any suitable type of Ethernet network, for example, via telecommunications/telephony networks such as analog voice networks or digital fiber communications networks, via storage area networks such as Fiber Channel SANs, or via any other suitable type of network and/or protocol, including WAN, LAN, Wi-Fi®, Bluetooth®, and/or the like.

The processor 320 is communicatively connected to the I/O module 350. The I/O module 350 is communicatively connected to the interface 124. According to one or more aspects, the I/O module 350 can be connected to other devices, either wired or wirelessly, including input peripherals such as keyboards, microphones, cameras, and/or the like.

Example Process(es)

To enable the reader to obtain a clear understanding of the technological concepts described herein, the following process(es) describes specific steps performed in a specific order. However, one or more of the steps of a particular process may be rearranged and/or omitted while remaining within the contemplated scope of the technology disclosed herein. One or more processes and/or steps thereof, may be combined, recombined, rearranged, omitted, or executed in parallel to create different process flows that are within the contemplated scope of the technology disclosed herein. While the process(es) below may omit or briefly summarize some of the details of the technologies disclosed herein for clarity, the details described in the paragraphs above may be combined with the process steps described below to get a more complete and comprehensive understanding of this (these) process(es) and the technologies disclosed herein.

Figure 4:
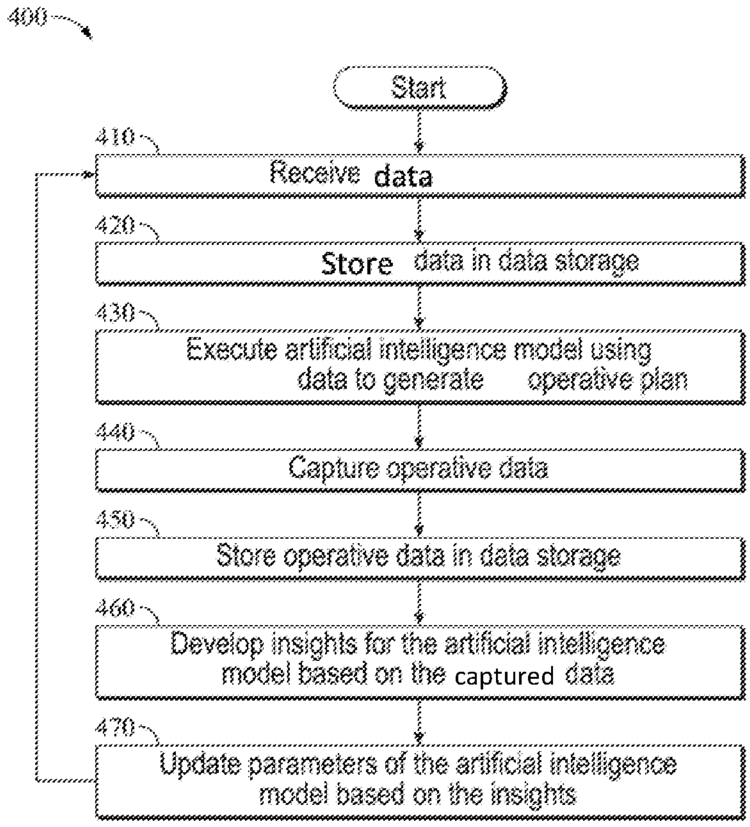
FIG. 4 illustrates a flowchart of a preoperative planning process, according to one or more aspects.

FIG. 4 illustrates a flow diagram of a process 400 of the operation of the surgical planning or assessment system 100. According to one or more aspects, and in reference to FIGS. 1, 2, 3, and 4, the process 400 begins at Start, in which the processor 320 commences the execution of the application 334 and moves on to perform step 410, where the computing device 310 receives data in response to the user 210 inputting data and/or calling data from data storage 312. Next, on step 420, data that is not stored in the data storage 312 (for example, data that does not have a copy of such data stored in the server data storage 112 and/or the device data storage 122) is stored in the data storage 312. Next, on step 430, the application 334 prepares the data (for example, via standardization and/or normalization) and executes the artificial intelligence module 338 with the data as input to the artificial intelligence module 338. In step 440, the data of the surgical procedure or assessment is captured as input from the user 210 (for example, via the interface 124) and/or as digital input from the camera 126/226. According to one or more aspects, the user 210 of step 410 is not the same person as the user 210 of the step 440. In step 450, the data captured on step 440 is stored in the data storage 312. Next, on step 460, the application 334 develops insights for the artificial intelligence model implemented by the artificial intelligence module 338 based on the data. Next, on step 470, the application 334 updates parameters of the artificial intelligence model based on the insights. The parameters of the artificial intelligence model include, for neural networks models: weights, number of layers, number of inputs, number of outputs, standardization and/or normalization algorithms, node activation functions, thresholds, and/or the like. As a nonlimiting example, in some embodiments the user 210 may upload a preoperative X-Ray image(s) and/or data via a network 130 such that the application 334 may predict the implant sizes necessary for surgery. As an additional and/or alternate example, in some embodiments the user 210 may upload a preoperative, intraoperative, or post-operative X-Ray image(s) and/or data via a network 130 of an implant within the patient such that the application 334 may predict the orientation and/or position of the implant. As an additional and/or alternate example, in some embodiments the user 210 may upload an intraoperative image of an implant or medical instrument 224 such that the application 334 may predict the orientation and/or position of the implant or medical instrument 224. As a nonlimiting example, in some embodiments the artificial intelligence model can include a DenseNet convolutional neural network architecture. A DenseNet is a type of convolutional neural network that utilizes dense connections between layers, through Dense Blocks, where all layers are connected with each other. Weights and layers having a near-zero multiplier will be identified as contributing near-zero, or having limited impact, in the final output of the artificial intelligence model. To reduce computational strain, these multiplications, layers, and connections can be subsequently removed from the neural network architecture and re-trained with the new architecture. As a result, the resulting convolutional neural network architecture may resemble that of different architectures. As an example, a residual neural network architecture is a similar neural network architecture where it utilizes skip connection over some layers. Meanwhile, a DenseNet architecture connects all layers. It is feasible that after eliminating the near-zero layers from the DenseNet, it would resemble that of a residual neural network architecture. Alternatively, the DenseNet may be adjusted to similarly resemble that of differently described neural network architectures. Alternatively, a different convolutional neural network architecture may be used. Separately, depending on the amount of data and accuracy of the artificial intelligence models will determine the model used for that user. As an example, a user having only a few examples may experience greater accuracy/generalizability with a different machine learning model, as opposed to a deep-learning model. Further, a confidence value may be provided as an output of several artificial intelligence models. When the user uploads the patient data to the server and executes the artificial intelligence model, several artificial intelligence models may be run. The output associated with the most confident and narrow prediction may be shown to the user to allow for the most confident output to be displayed. If the model is specific to the user, two model outputs may be shown: the model output specific to the user's history and preference, and a second output trained on all users. As an example, if a user has several thousand cases used to train an artificial intelligence model, they are more likely to have an artificial intelligence model specific to them that may be more accurate and with greater confidence to predict their operative outcomes when compared to an artificial intelligence model trained on all users. In that scenario, the user may receive feedback from an artificial intelligence model specifically trained from their patient history, and/or from an artificial intelligence model trained from all users.

The steps and actions of the system 100 described in connection with the aspects disclosed herein may be embodied directly in hardware, in a software module (such as the application 334 parts or components of the application 334, and/or the data storage 312) executed by a processor (such as the processor 320), or in a combination of the two. The software module may reside in the cache of the processor 320 and/or in the memory 330, which may be RAM, flash memory, ROM memory, EPROM memory, EEPROM memory, registers, a hard disk, a removable disk, a CD-ROM, and/or any other form of storage medium known in the art. An exemplary storage medium may be coupled to the processor 320 such that the processor 320 can read information from, and write information to, the storage medium. In the alternative, the storage medium may be integrated into the processor 320. Further, according to one or more aspects, the processor 320 and the storage medium may reside in an Application Specific Integrated Circuit (ASIC). In the alternative, the processor and the storage medium may reside as discrete components in a computing device. Additionally, according to one or more aspects, the events or actions of a method or algorithm may reside as one or any combination or set of codes and instructions on a machine-readable medium or computer-readable medium, which may be incorporated into a computer program product.

Also, any connection may be associated with a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. "Disk" and "disc," as used herein, include compact disc (CD), laser disc, optical disc, digital versatile disc (DVD), floppy disk and Blu-ray disc where disks usually reproduce data magnetically, while discs usually reproduce data optically with lasers. Combinations of the above should also be included within the scope of computer-readable media.

In some embodiments, the system 100 is world-wide-web (www) based, and the server 110 is a web server delivering HTML, XML, JSON, data, web pages, etc., to computing devices. In other embodiments, a client-server architecture may be implemented, in which a network server executes enterprise and custom software, exchanging data with custom client applications running on the computing device.

It will be understood that it would be unduly repetitious and obfuscating to describe and illustrate every combination and subcombination of the elements and the aspects described. Accordingly, all elements can be combined in any way and/or combination, and the present specification, including the drawings, shall be construed to constitute a complete written description of all combinations and subcombinations of the elements and of the aspects described herein, and of the manner and process of making and using them, and shall support claims to any such combination or subcombination.

An equivalent substitution of two or more elements can be made for any one of the elements in the claims below or that a single element can be substituted for two or more elements in a claim. Although elements can be described above as acting in certain combinations and even initially claimed as such, it is to be expressly understood that one or more elements from a claimed combination can in some cases be excised from the combination and that the claimed combination can be directed to a subcombination or variation of a subcombination.

It will be appreciated by persons skilled in the art that what has been particularly shown and described hereinabove is not limiting and is not to be interpreted as foreclosing modifications and variations. A variety of modifications and variations are possible in light of the above teachings without departing from the following claims.

What is claimed is:

1. A computerized surgical planning process stored in memory that when executed by a processor performs steps comprising:

receiving, via input from a user on an electronic device, patient data comprising patient information and at least one image of patient anatomy;

receiving a user identity associated with a surgeon performing a surgical procedure;

storing the patient data and the user identity in a data storage;

generating, by executing a multimodal artificial intelligence model using the patient data as input and applying learned model parameters associated with the user identity, a prediction of a surgeon-specific implant parameter, wherein the surgeon-specific implant parameter comprises an implant size, an implant orientation, or both, and wherein the learned model parameters associated with the user identity adjust the surgeon-specific implant parameter based on historical tendencies associated with the surgeon;

capturing operative data resulting from the surgical procedure, wherein the operative data comprises an actual implant parameter utilized by the surgeon during the surgical procedure;

storing the operative data in the data storage; and updating parameters of the artificial intelligence model based on the operative data, wherein updating the parameters includes adjusting the learned model parameters associated with the user identity based on a comparison between the predicted surgeon-specific implant parameter and the actual implant parameter utilized by the surgeon.

2. The computerized surgical planning process of claim 1, wherein the operative data comprises user feedback identifying an implant size actually implanted during the surgical procedure.

3. The computerized surgical planning process of claim 1, wherein at least one of the server or the electronic device includes the data storage; and wherein the executing the multimodal artificial intelligence model occurs via at least one of the server or the electronic device.

4. The computerized surgical planning process of claim 1, wherein the surgical procedure includes cutting tissue for receiving at least one of an implant or a prosthesis.

5. The computerized surgical planning process of claim 4, wherein generating the prediction comprises identifying, from the at least one image of patient anatomy, a predicted implant-size range including one or more candidate sizes for at least one implant or prosthesis based on a contour of the patient's bone, without requiring the user to independently select among implant sizes.

6. The computerized surgical planning process of claim 5, wherein at least one of the server or the electronic device includes the data storage; and wherein the executing the multimodal artificial intelligence model occurs via at least one of the server or the electronic device.

7. The computerized surgical planning process of claim 6, wherein the data comprises at least one of an image or patient information.

8. The computerized surgical planning process of claim 7, wherein the artificial intelligence model is trained to generate at least one of the prediction or an operative plan based on training data; and wherein the operative plan comprises:

a list of medical instruments for use during the surgical procedure; and/or a list of surgical steps to perform the surgical procedure, wherein each surgical step is associated with one or more of the medical instruments from the list of medical instruments.

9. A computerized surgical planning system comprising:

an electronic device with an interface configured to receive input from a user, the input including patient data comprising patient information and at least one image of patient anatomy;

a server that receives the data;

a data storage that stores the data;

a memory storing an application;

a processor which executes the application to cause the system to:

receive, via input from a user, the patient data;

receive a user identity associated with a surgeon performing a surgical procedure;

store the patient data and the user identity in the data storage;

generate, by executing a multimodal artificial intelligence model using the patient data as input and applying learned model parameters associated with the user identity, a prediction of a surgeon-specific implant parameter, wherein the surgeon-specific implant parameter comprises an implant size, an implant orientation, or both, and wherein the learned model parameters associated with the user identity adjust the surgeon-specific implant parameter based on historical tendencies associated with the surgeon;

capture operative data resulting from the surgical procedure, wherein the operative data comprises an actual implant parameter utilized by the surgeon during the surgical procedure;

store the operative data in the data storage; and update parameters of the artificial intelligence model based on the operative data, wherein updating the parameters includes adjusting the learned model parameters associated with the user identity based on a comparison between the predicted surgeon-specific implant parameter and the actual implant parameter utilized by the surgeon.

10. The computerized surgical planning system of claim 9, wherein the operative data comprises user feedback identifying an implant size actually implanted during the surgical procedure.

11. The computerized surgical planning system of claim 9, wherein at least one of the server or the electronic device includes the data storage; and wherein the executing the multimodal artificial intelligence model occurs via at least one of the server or the electronic device.

12. The computerized surgical planning system of claim 9, wherein the surgical procedure includes cutting tissue for receiving at least one of an implant or a prosthesis.

13. The computerized surgical planning system of claim 12, further comprising generating the prediction comprises identifying, from the at least one image of patient anatomy, a predicted implant-size range including one or more candidate sizes for at least one implant or prosthesis based on a contour of the patient's bone, without requiring the user to independently select among implant sizes.

14. The computerized surgical planning system of claim 13, wherein at least one of the server or the electronic device includes the data storage; and wherein the executing the multimodal artificial intelligence model occurs via at least one of the server or the electronic device.

15. The computerized surgical planning system of claim 14, wherein the operative data comprises user feedback identifying an implant size actually implanted during the surgical procedure.

16. The computerized surgical planning system of claim 15, wherein at least one of the server or the electronic device includes the data storage; and wherein the executing the multimodal artificial intelligence model occurs via at least one of the server or the electronic device.

17. A non-transitory computer readable medium having computer readable instructions executable by a processor which, when executed, performs a process for generating a prediction of a surgeon-specific implant parameter for a surgical procedure, the process comprising:

receiving, via input from a user, patient data comprising patient information and at least one image of patient anatomy;

receiving a user identity associated with a surgeon performing a surgical procedure;

storing the patient data and the user identity in a data storage;

generating, by executing a multimodal artificial intelligence model using the patient data as input and applying learned model parameters associated with the user identity, a prediction of a surgeon-specific implant parameter, wherein the surgeon-specific implant parameter comprises an implant size, an implant orientation, or both, and wherein the learned model parameters associated with the user identity adjust the surgeon-specific implant parameter based on historical tendencies associated with the surgeon;

capturing operative data resulting from the surgical procedure, wherein the operative data comprises an actual implant parameter utilized by the surgeon during the surgical procedure;

storing the operative data in the data storage;

updating parameters of the artificial intelligence model based on the operative data, wherein updating the parameters includes adjusting the learned model parameters associated with the user identity based on a comparison between the predicted surgeon-specific implant parameter and the actual implant parameter utilized by the surgeon.

18. The non-transitory computer readable medium of claim 17, wherein the surgeon-specific implant parameter comprises the implant orientation, and wherein the actual implant parameter is captured intraoperatively or postoperatively via an imaging device, a camera, or coordinate information generated from image data captured by the imaging device or the camera.

19. The non-transitory computer readable medium of claim 18, wherein the at least one image of patient anatomy comprises a preoperative x-ray, a preoperative CT image, a preoperative MRI image, a preoperative or intraoperative ultrasound image, or a preoperative or intraoperative optical image.

20. The non-transitory computer readable medium of claim 19, wherein capturing the operative data comprises receiving user feedback entered after the surgical procedure without requiring direct data capture from within an operating room.

* * * * *